United States Patent [19]

Melton, Jr. et al.

[11] Patent Number: 5,195,521

[45] Date of Patent: Mar. 23, 1993

[54] TISSUE MEASUREMENTS

[75] Inventors: Hewlett E. Melton, Jr., Sunnyvale, Calif.; Thomas A. Shoup, Lowell, Mass.

[73] Assignee: Hewlett-Packard Company, Palo Alto, Calif.

[21] Appl. No.: 614,780

[22] Filed: Nov. 9, 1990

[51] Int. Cl.$^5$ .............................................. A61B 8/00
[52] U.S. Cl. ........................... 128/660.02; 128/661.10; 128/661.04
[58] Field of Search ...................... 128/660.02, 661.04, 128/661.10; 73/861.25

[56] References Cited

U.S. PATENT DOCUMENTS

| | | | |
|---|---|---|---|
| 4,483,345 | 11/1984 | Miwa | 128/660.02 |
| 4,501,277 | 2/1985 | Hongo | 128/661.04 |
| 4,733,668 | 3/1988 | Torrence | 128/660 |
| 4,790,322 | 12/1988 | Iinuma | 128/661.10 |
| 4,807,636 | 2/1989 | Skidmore et al. | 128/661.10 |
| 4,913,159 | 4/1990 | Gardin et al. | 128/661.10 |

OTHER PUBLICATIONS

Rational Gain Compensation for Attenuation in Cardiac Ultrasonography by Hewlett E. Melton, Jr. & David J. Skorton/Pub.:Ultrasonic Imaging 5,214–228 (1983).

Automatic Real-Time Endocardial Edge Detection in Two-Dimensional Endocardiography by Hewlett E. Melton, Jr., Steve M. Collins & David J. Skorton/Pub.-:Ultrasonic Imaging 5, 300–307 (1983).

Primary Examiner—Francis Jaworski
Assistant Examiner—George Manuel

[57] ABSTRACT

A system for deriving signals representing a selected cross sectional area and volume of a region of interest in tissue. In the preferred embodiment, area and volume of a fluid filled cavity contained in tissue on a real time basis are determined by launching pulses of ultrasonic pressure waves along a plurality of scan lines, detecting the locations along each line that are in fluid, deriving a signal representing the incremental area within fluid that is between adjacent scan lines, deriving a signal representing the cross sectional area of a cavity within a region of interest by summing the incremental areas and deriving a signal representing the volume of the cavity within a region of interest by revolving each incremental area about an axis of the cavity so as to form an incremental volume of revolution and summing the volume of revolution. The volume of then entire cavity is also attained by deriving the cross sectional area as just described, raising it to the 3/2 power and multiplying it by a coefficient including a function of the ratio of the long axis cross sectional area and short axis cross sectional area. Determination of the locations in fluid in the above calculations are preferably those at which a majority of an odd number of consecutive scan lines at like ranges are in fluid.

28 Claims, 10 Drawing Sheets

FIG.2D SOF

FIG.2E SOL

FIG.2F Is

FIG.2G CTR | 3 | 2 | 1 | 0 | | 3 | 2 | 1 | 0 |

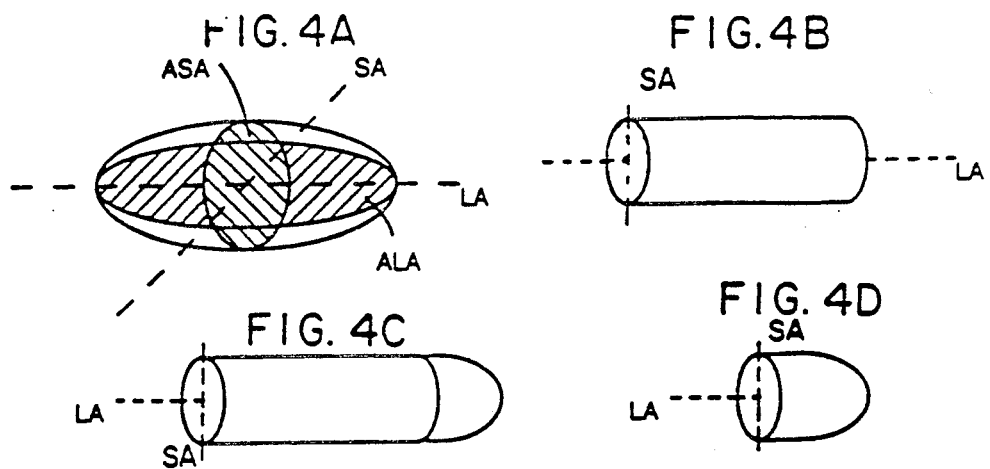
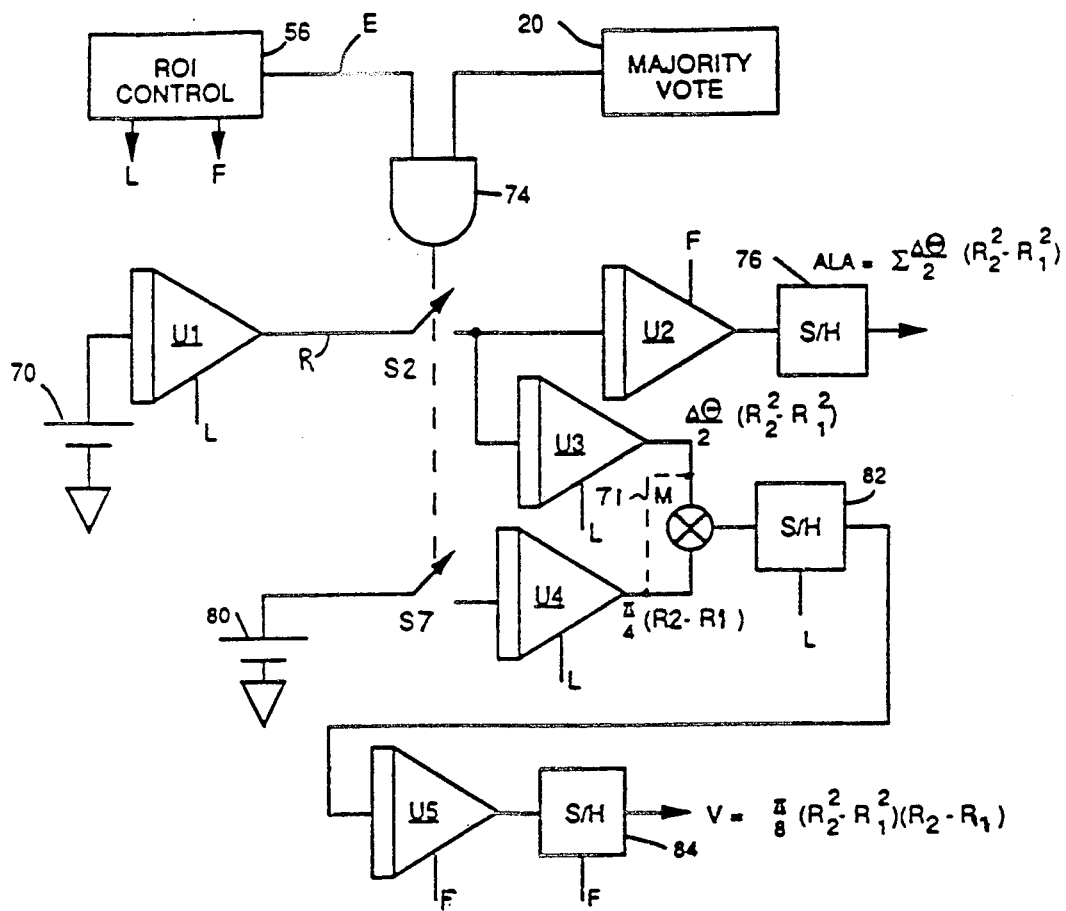
FIG. 5
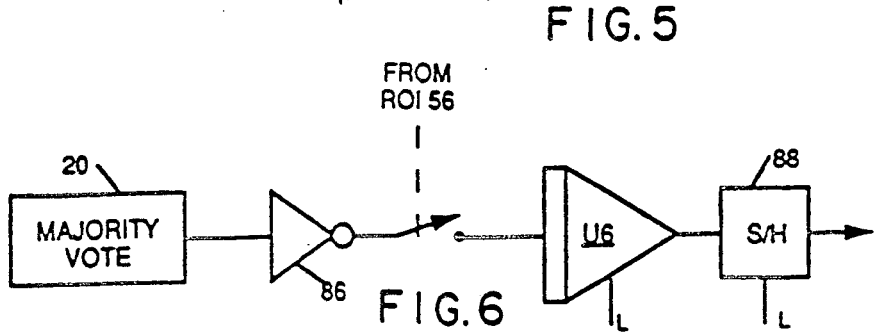
FIG. 6

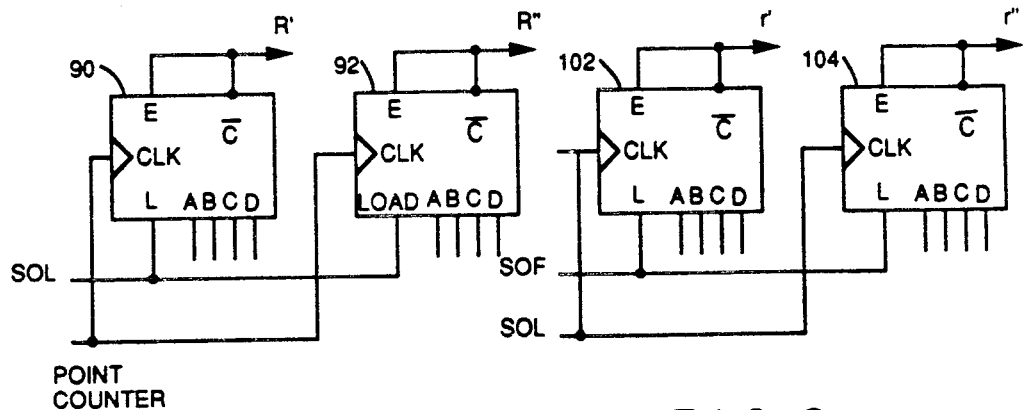
FIG. 7   FIG. 8

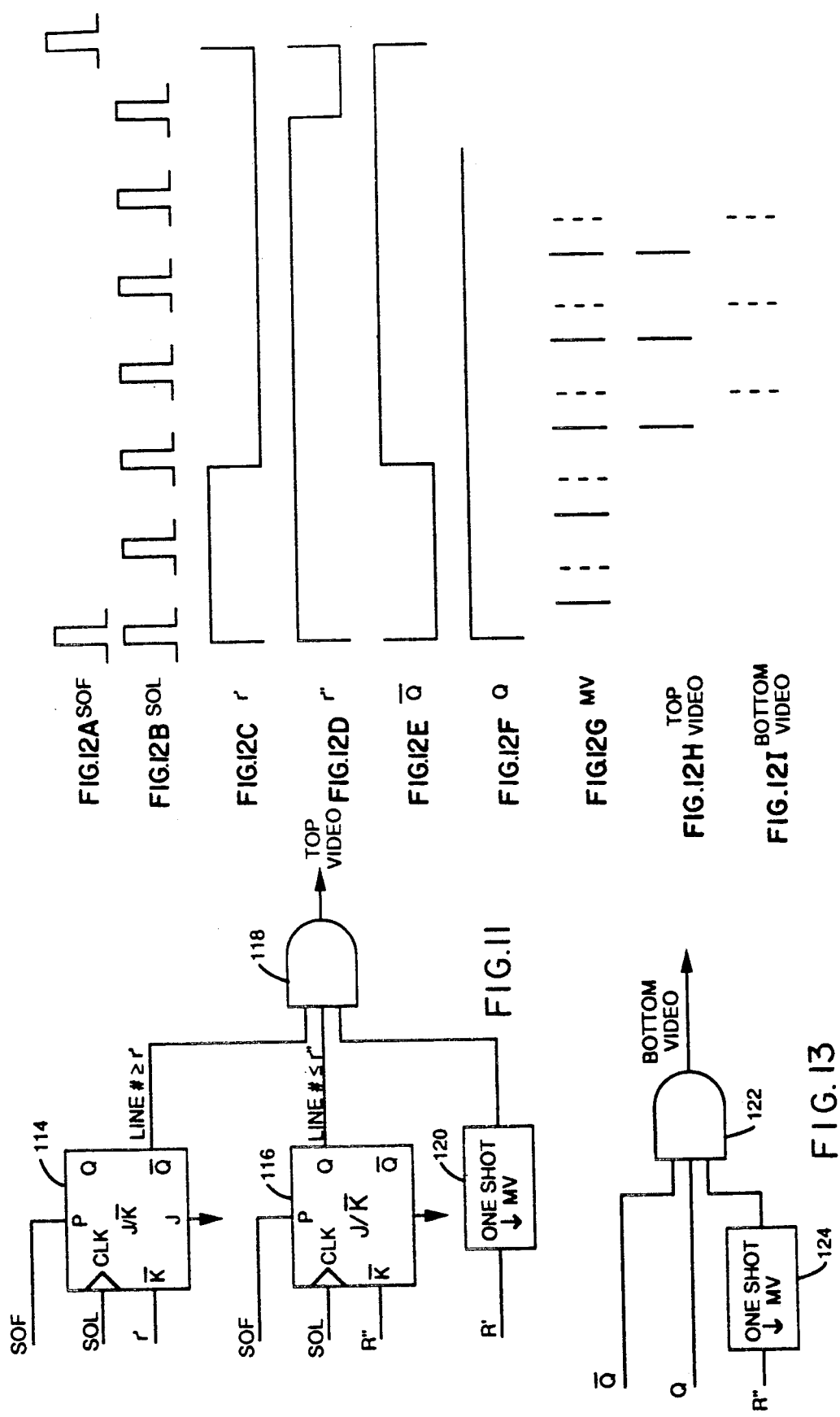

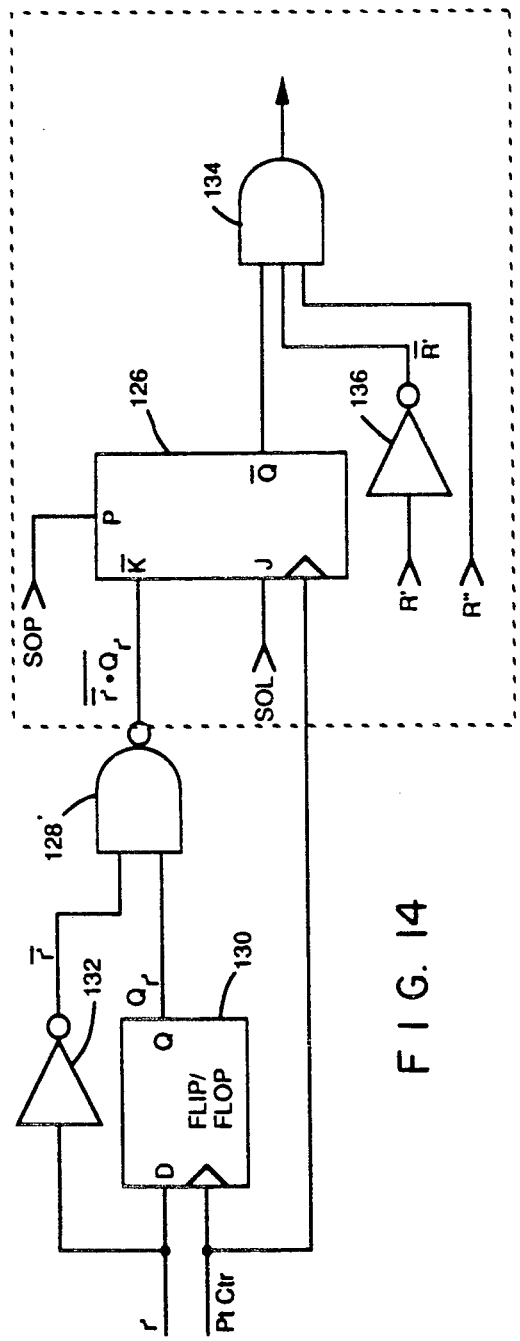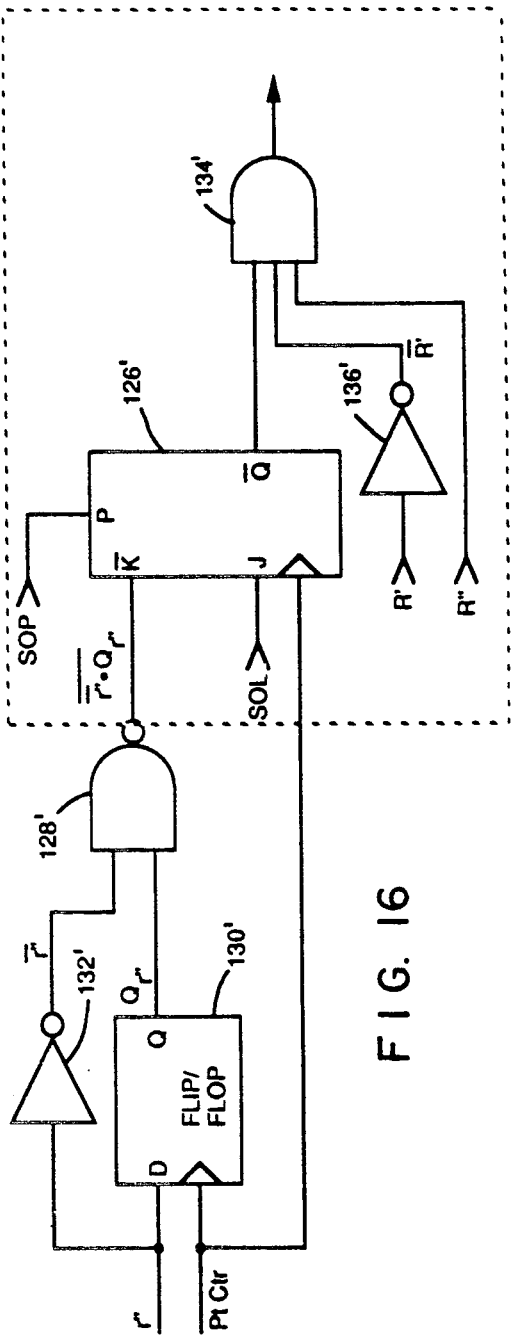
FIG. 14
FIG. 16

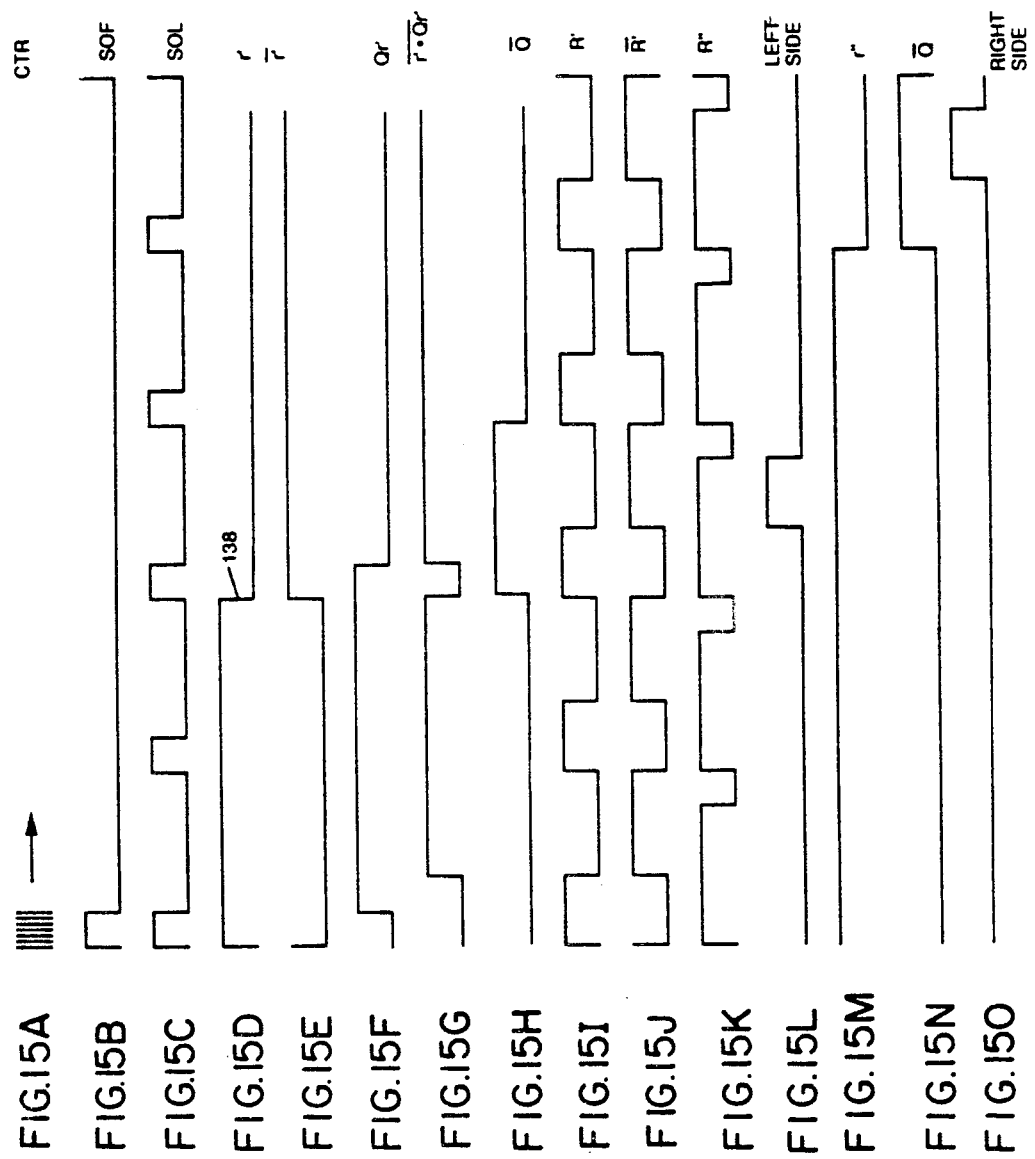

TISSUE MEASUREMENTS

BACKGROUND OF THE INVENTION

Measurement of the cross sectional area of a body cavity such as a blood filled ventricle of a heart is useful for monitoring its operation, and measurement of its volume is useful in determining physiological factors such as stroke volume, cardiac output and the ejection fraction. At present, measurements of cross sectional area and volume are not attainable on a real time basis without the use of invasive procedures such as catheterization techniques in which foreign substances are injected into the bloodstream. Because of the risks involved, these procedures are not used to monitor patients on a continuing basis.

Off line non-invasive methods for measuring a cross sectional area of a ventricle are known, but they are laborious and time consuming. In one, the cross sectional area of a ventricle appearing in successive frames by an ultrasonic imaging apparatus is measured by hand. In another method, the edge of a cross sectional area in one frame is drawn by hand and optical flow techniques are used to identify the location of the edge in successive frames. Whereas this outlines the cross sectional areas more rapidly than can be done by hand, the areas are still measured manually.

In employing the optical flow techniques it is necessary to provide a tissue indicator for indicating where the edges of a ventricle occur. A circuit for this purpose is described in an article entitled *Automatic Real Time Endocardial Edge Detection In Two Dimensional Endiocardiography* at pages 303-307 of Ultrasonic Imaging 5, 1983, and incorporated herein by reference. In this circuit a reference voltage having a value between the higher amplitude expected of image signals caused by reflections from tissue and the lower amplitude expected of image signals caused by reflection from blood is applied to one input of a comparator, and the image signals are applied to the other. Thus, the output of the comparator may be 1 for signals derived from reflections from tissue and 0 for signals derived from reflections from blood so that a change from 1 to 0 or from 0 to 1 indicates the presence of an edge. A one bit filter such as described in the article noted below that relates to rational gain control is connected to the output of the comparator so as to provide a signal that changes state only when the output of the comparator has changed state for a given length of time.

There is another problem however. As is well known, the amplitude of the reflections from structures within the body decreases with range because of absorption of the energy from the transmitted pressure waves as they pass through the body. Thus it is possible for the amplitude of the image signals due to reflections from tissue on the far side of the ventricle to become less than the reference voltage referred to above and thereby fail to cause the change in the comparator output that would indicate the location of the far edge. For this reason, it has been customary to gradually increase the gain of the amplifier to which the image signals are applied after each pulse is transmitted. It has been suggested that improved results can be obtained by using a rational gain control circuit, RGC, that increases the gain of the amplifier more rapidly when the comparator of the edge detector circuit indicates that the image signals are due to reflections from tissue than when it indicates that the reflections are from blood. Such a circuit is described in an article entitled *Rational Gain Compensation For Attenuation In Cardiac Ultrasonography* at pages 214-228 of Ultrasonic Imaging 5, 1983, and incorporated herein by reference. Unfortunately, however, noise spikes can still cause the comparator to change its output so as to give a false indication of the position of a edge.

BRIEF SUMMARY OF THE INVENTION

In deriving the values of cross sectional area and/or volume of a region of one type of matter contiguous with a different type of matter, e.g. blood within a heart ventricle, the accuracy of the results depends on proper identification of the edges of the region. In accordance with the invention, signals from a scanner or from a recording of such signals are processed before application to on input of a comparator so as to statistically provide greater probability that the signals correspond to one type of matter or the other. The processing can be accomplished in different ways that usually are some form of integration. Although other types of processing can be used, the following provide some measure of improvement: deriving a signal representing integrated backscatter; video detection, filtering the r.f.; integration of data from various pixels; and deriving a signal representing the statistics of the A.C. signal. At present, the most effective procedure is the derivation of a signal representing the integrated backscatter.

Regardless of the processing used, greater accuracy in defining the border between different types of matter is achieved in accordance with a further aspect of the invention by coupling the output of the comparator to a circuit that provides a signal corresponding to the state the output of the comparator had at corresponding pixels in previous scan lines. The circuit will be referred to as a majority vote circuit.

This invention provides apparatus and method for non-invasively deriving signals, in real time, that are indicative of the cross sectional area of a fluid filled cavity such as a blood filled ventricle of a heart as well as signals indicative of its volume. As in the prior art, an ultrasonic scanner is used to successively transmit pulses of ultrasonic pressure waves along scan lines passing through a desired cross section of the heart, and the image signals derived from reflections of the pressure waves at points along each scan line are applied to a blood/tissue indicator circuit that produces different signals depending on whether the electrical waves are responsive to reflections from blood or are responsive to reflections from tissue. If a scan line successively passes through the near wall of the ventricle of the heart, through the cavity in the ventricle containing blood and then through the far wall, the signal will change from a first value such as 1 to a second value such as 0 at the edge of the near inner wall and then change back to the first value 1 at the range of the far inner wall.

In accordance with a basic aspect of this invention, a signal is provided that can be integrated following the start of a scan line so as to derive a value representing the area between the current scan line and the previous one, and the integration is effectively performed only while reflections of the transmitted pulses are from blood, as indicated by the blood/tissue circuit, so as to derive signals respectively representing the incremental blood filled areas between adjacent scan lines. The latter signals are then summed to derive a signal representing the cross sectional area of the ventricle. In view of the fact that this process can be completely performed at the same rate with which images are formed, the signal representing the cross sectional area follows the real time changes occurring therein during a heart cycle.

In one embodiment of the invention, a real time signal representing the volume of the ventricle is derived from the signal representing its cross sectional area by raising the latter signal to the three halves power and multiplying by coefficients including a function of the ratio between the long axis and short axis cross sectional areas as well as other factors that depend on an assumed shape for the ventricle. The ratio between the two cross sectional areas can be approximated by an experienced cardiologist or it can be determined by measurement.

In another embodiment of the invention, a circuit and method are provided for determining in accordance with Simpson's rule, the volume of a fluid filled cavity such as a heart ventricle on a real time basis. It is arranged that the scan lines along which ultrasonic pulses are propagated intersect the long axis, LA, of the ventricle at approximately 90°. Each of the previously mentioned blood filled incremental areas that lie between adjacent scan lines is effectively rotated about the long axis LA so as to form an incremental volume of revolution, and the total volume of the ventricle is derived by summing the incremental volumes.

As is known by those familiar with images produced from signals derived by an ultrasonic scanner, some of the scan lines may extend through a ventricle that is not of interest as well as through a ventricle for which signals representing cross sectional area and volume are desired. As this would cause the signals representing incremental cross sectional areas to include incremental areas of the ventricle that is not of interest, means are provided in accordance with another aspect of this invention for controllably outlining in the image a region of interest, ROI, that only includes a cross section of the ventricle of interest and for limiting the calculation of the incremental areas to the portion of a blood filled ventricle appearing within ROI.

In accordance with another aspect of this invention, the accuracy of the signals representing the incremental areas is improved by using what will be called a majority vote circuit that indicates at each range along a current scanned line when the majority of the signals of the tissue/blood circuit for the current line and two previous lines indicate that the reflections of the transmitted pulses are from tissue or blood. Increased accuracy is obtained because the majority vote is less affected by noise spikes than the output of the tissue/blood circuit.

The accuracy of the location of edges is increased in accordance with another feature of the invention by deriving from the r.f. signal at the output of the scanner or a recording thereof a signal representing a characteristic of matter such as the amplitude of the integrated backscatter, applying that signal to the tissue/blood detection circuit and using a reference value in the detection circuit that is between the value of integrated backscatter expected from tissue and the value of integrated backscatter expected from blood. A circuit for deriving a signal representing integrated backscatter is described in U.S. Pat. No. 4,873,984 issued on Oct. 17, 1989 in the name of Thomas J. Hunt, et al, entitled *Techniques For Calculating Ultrasonic Integrated Backscatter Using Frequency or Time Domain Techniques*, and incorporated herein by reference.

Another feature of this invention provides means for indicating the edges between tissue and blood in an M mode display.

In accordance with still another feature of this invention an edge marker circuit is provided that changes the brightness produced in a 2D image of the cross sectional area along the inner walls of a fluid filled cavity such as a ventricle containing blood.

BRIEF DESCRIPTION OF THE DRAWINGS

FIGS. 2D–2G are related timing diagrams illustrating the operation of FIG. 2C.

FIG. 4A–4D illustrate various assumed shapes for a ventricle.

FIG. 5 is a schematic diagram of a circuit for calculating the volume of a ventricle in accordance with Simpson's rule.

FIG. 6 is schematic diagram of a circuit used for M mode operation.

FIG. 7 is a counter circuit for generating signals R' and R" respectively representing the inner and outer radii of a region of interest, ROI.

FIG. 8 is a schematic diagram of a counter circuit for generating signals r' and r" that respectively occur during the scanning of radial lines on opposite sides of ROI.

FIGS. 9 and 9A–9D are related timing diagrams illustrating the operation of the circuit of FIG. 7.

FIGS. 10A–10D are related timing diagrams illustrating the operation of FIG. 8.

FIG. 11 is a schematic diagram of a circuit for generating signals for forming the top border of ROI.

FIGS. 12A–12I are related timing diagrams illustrating the operation of FIG. 11 and FIG. 13.

FIG. 13 is a schematic diagram of a circuit for generating signals for forming the bottom border of ROI.

FIG. 14 is a schematic diagram of a circuit for generating signals for forming the border of ROI that is closer to the first scanned line of a frame.

FIGS. 15A–15O are related timing diagrams illustrating the operation of FIGS. 14 and 16.

FIG. 16 is a schematic diagram of a circuit for generating signals for forming the border of ROI that is closer to the last scanned line of a frame.

DETAILED DESCRIPTION OF A PREFERRED EMBODIMENT

Figure 1:
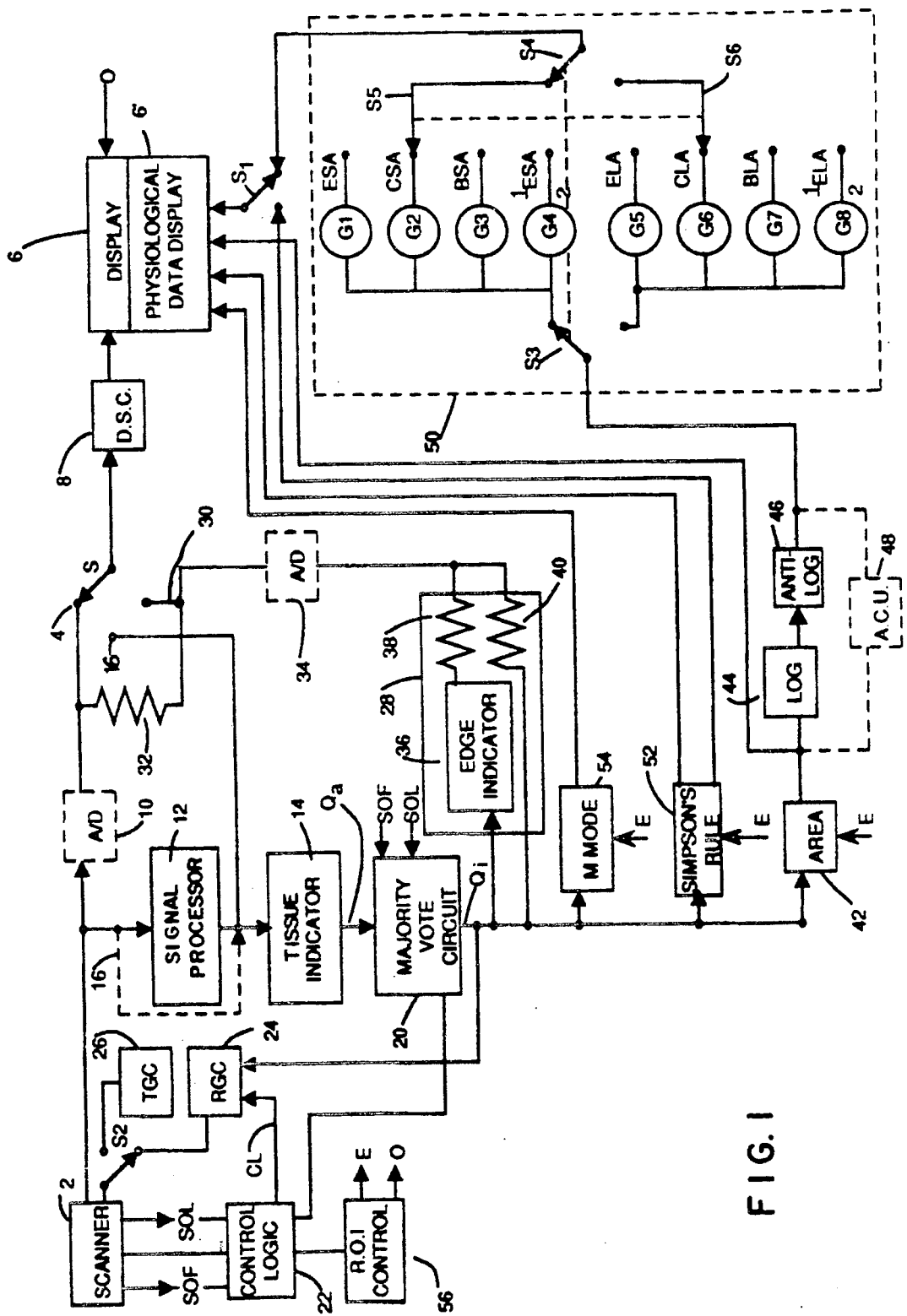
FIG. 1 is a block diagram of an ultrasonic system embodying this invention.

Reference is made to a block diagram of FIG. 1 for an overview of a system incorporating the invention. Details of certain blocks of FIG. 1 will be described subsequently.

A scanner 2 transmits pulses of ultrasonic pressure waves into a patient's body along successive scan lines that may be parallel or radial and produces electrical signals in response to their reflections from reflectors along each line. The electrical signals can be analog or digital forms of r.f. or video. Whether the signals are analog or digital, they can be coupled via a contact 4 of a switch S to a suitable display means 6 so as to produce a 2D image of a cross section in the usual manner, but if the scan lines along which the pressure waves travel are radii, it is preferable to use a scan converter 8 so as to derive signals that can be used by a parallel line TV type raster display. If the signals are analog, it may be preferable to convert them to digital form with an A/D converter 10 so that the scan converter 8 can be digital.

In order to improve the accuracy with which the edge of a ventricle is identified, it is preferable to apply the electrical signals to a signal processor circuit 12 for producing a signal which, in this embodiment represents integrated backscatter and applying it to a tissue indicator circuit 14. A dashed line 16 indicates the direct application of the signals from the scanner 2 to the tissue indicator circuit 14 when the integrated backscatter circuit 12 is not used.

A majority vote circuit 20 that is an important aspect of this invention produces at each range a signal indicative of whether the signal provided by the tissue/blood detector 14 represents tissue or blood at that range for a majority of consecutive scan lines including the line currently being scanned. Thus, if the indicator circuit 14 outputs for a majority of the lines a signal indicating that reflections at a range are from tissue, the majority vote circuit 18 outputs a signal indicative of the fact that the reflections are from tissue, and if the indicator circuit 14 outputs a different signal for a majority of lines, the majority vote circuit 20 outputs another signal indicative of the fact that the reflections are from blood. The majority vote circuit 20 is controlled by a controller 22 that is coupled to receive line and frame reset pulses from the scanner 2.

A rational automatic gain control circuit 24, RGC, as described in the article referred to in the description of the background of the invention, responds to the signal provided by the majority vote circuit 20 so as to increase the gain of the scanner 2 more rapidly with time when the circuit 20 indicates that the signals are due to reflections from tissue than it does when the circuit 20 indicates that the signals are due to reflections from blood. Although the RGC circuit 24 is preferred, a TGC circuit 26 that increases the gain with range can be coupled to control the gain of the scanner 2 if desired.

An edge marker circuit 28 responds to a change in the signal provided by the majority vote circuit 20 between tissue and blood and vice versa to produce short pulses that can be used to form an outline of any cavities or ventricles in an image presented by the display means 6. If the outline is to be superimposed on the 2D image, the pulses can be coupled to the contact 4 of the switch S via a switch contact 30 and a resistor 32 and can be converted to digital form, if required, by an A/D converter 34. If the outline is to be presented by itself, the arm of the switch S is connected to the contact 30.

The edge marker circuit 28 includes an edge indicator circuit 36 that outputs a high logic level for a brief interval such as one microsecond whenever the output of the majority vote circuit 20 changes from a high level to a low level or vice versa. A resistor 38 is coupled between the output of the edge indicator circuit 36 and the contact 30 of the switch S, and a resistor 40 is coupled between the output of the majority vote circuit 20 and the contact 30. When, for example, successive signals from the majority vote circuit 20 are 0, as may be the case when the reflections of the transmitted pulses of pressure waves are from blood, a voltage of zero is applied to the terminal 30; when successive signals from the circuit 20 are 1, as may be the case when the reflections are from tissue, the voltage will be somewhat higher as determined by the value of the resistor 40, and when successive signals from the circuit 20 change from 1 to 0 or vice versa, a maximum voltage is applied to the contact 30 because of the addition of the high logic level provided by the edge indicator circuit 36. Thus, when the switch S connects the terminal 4 to the display 6, blood can be displayed as being black, tissue as being gray, and the edges of the tissue as being white or some other grey level. A color scheme can also be used where blood is one color, tissue is another color and the edges yet another color.

A signal representing a cross sectional area of a ventricle is derived by a circuit 42 to be described and coupled, if desired, to a physiological data display section 6' of the display 6. By raising the signal representing the cross sectional area to the three halves power with a logging means 44 and an antilog means 46 or with an analog calculation unit 48, and multiplying the result by an appropriate coefficient, corresponding to the algorithm desired by the operator, that is selected by closure of the correct combination of switches contained in a dashed rectangle 50, a signal representing the volume of the ventricle may be produced that can be coupled to the physiological data display section 6' via a switch S1.

A circuit 52 derives a signal representing the cross sectional area of a ventricle that may be conducted to the display section 6', and it also derives a signal representing the volume of the ventricle by Simpson's rule that can be supplied to the display section 6' via the switch S1.

During M mode operation, a signal representing the portion of a single scan line that lies between the edges of a ventricle is derived by a circuit 54 and displayed on the means 6.

In order that the information derived by the circuits described above may pertain to a selected ventricle, an adjustable region of interest (ROI) control 56 supplies signals 0 that can be applied to the display means 6 so as to outline the region of interest. The ROI control 56 also supplies signals E that enable the circuits of the blocks 42, 52 and 54 to operate only in response to signals derived from reflections from points within ROI.

THE MAJORITY VOTE CIRCUIT

Figure 2A:
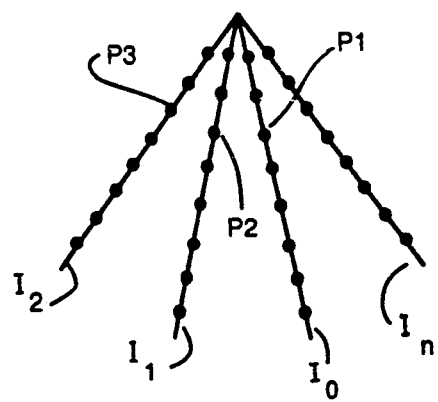
FIG. 2A illustrates the relationships between tissue/blood decisions that are subjected to a majority vote by the circuit of FIG. 2B.

Reference is now made to FIGS. 2A–G for a detailed description of one specie of the majority vote circuit 20. FIG. 2A includes three sequential lines in the middle of a sector scan $l_0$, $l_1$, and $l_2$ with $l_0$ being the current line as indicated by the scan direction arrow. The tissue indicator 14 of FIG. 1 outputs a signal Qa that is either a 1 or a 0 depending on whether the reflections of a transmitted pulse are from tissue or blood at correspondingly spaced ranges indicated by dots along the lines. When a signal from the tissue indicator 14 occurs at P1, the majority vote circuit of FIG. 2B determines whether the majority of the signals at points P1, P2 and P3, which are at the same range, are a 1 or a 0. Thus, if the signals from the tissue/blood circuit 14 at the points P1, P2 and P3 are 1,0,0 respectively, the majority vote circuit will indicate that the reflections producing P1 were from blood even though the tissue/blood circuit 14 indicates that at P1 they are from tissue. The opposite would be true if the signals were 0,1,1. Greater reliability is achieved in this manner.

The circuit of FIG. 2B carries out the operations just described in the following manner. The signal Qa from the tissue indicator circuit 14 of FIG. 1 for a given range R is applied to an input of a ROM 58 wherein it is compared with signals s1 and s2 that respectively represent the values of Qa for the range R of the two previous scan lines so as to derive a majority vote V. The vote V, which may be a 1 or a 0, is applied to a latch 60 and emerges therefrom as a signal Q'a. The signals applied to s1 and s2 were read from a RAM 62 and applied to s1 and s2 via conductors d1 and d2 respectively and a latch 64. During this reading, the ROM 58 is disabled and its outputs that are connected to d1 and d2 are set at a high impedance. After the vote has been taken by the ROM 58, the RAM 62 is placed in a write mode and the ROM 58 connects the Qa input to d1 so as to write the value of Qa in the same address in the memory of the RAM 62 from which the signal for s1 was previously read, and it also connects the signal at the input s1 via d2 to the same address in the memory of the RAM 62 from which the signal supplied to s2 was read. The signal originally at s2 is discarded. Thus, after each vote is taken, the values of Qa are shuffled as follows, Qa→s1, and the value of Qa at s1 is transferred to s2.

It will be apparent that a majority vote for the first two lines cannot be taken because there are only one or two lines. Therefore, it is preferable to use a signal provided by a line counter 70 during the first two lines to cause the signals Qa occurring during these two lines to appear at the output V. In other words, the tissue/blood decisions of the circuit 14 for the first two lines are used directly. The timer 70 is shown in more detail in FIG. 2C and operates as illustrated in the timing diagrams of FIGS. 2D–2G to generate a signal Is that causes the ROM 58 of FIG. 2B to operate as just described. The counter 70 is loaded at the start of a frame in response to start of frame pulses SOF with a count of 3 and clocked by start of line pulses, SOL, so as to generate the signal Is at its carry output.

Figure 2B:
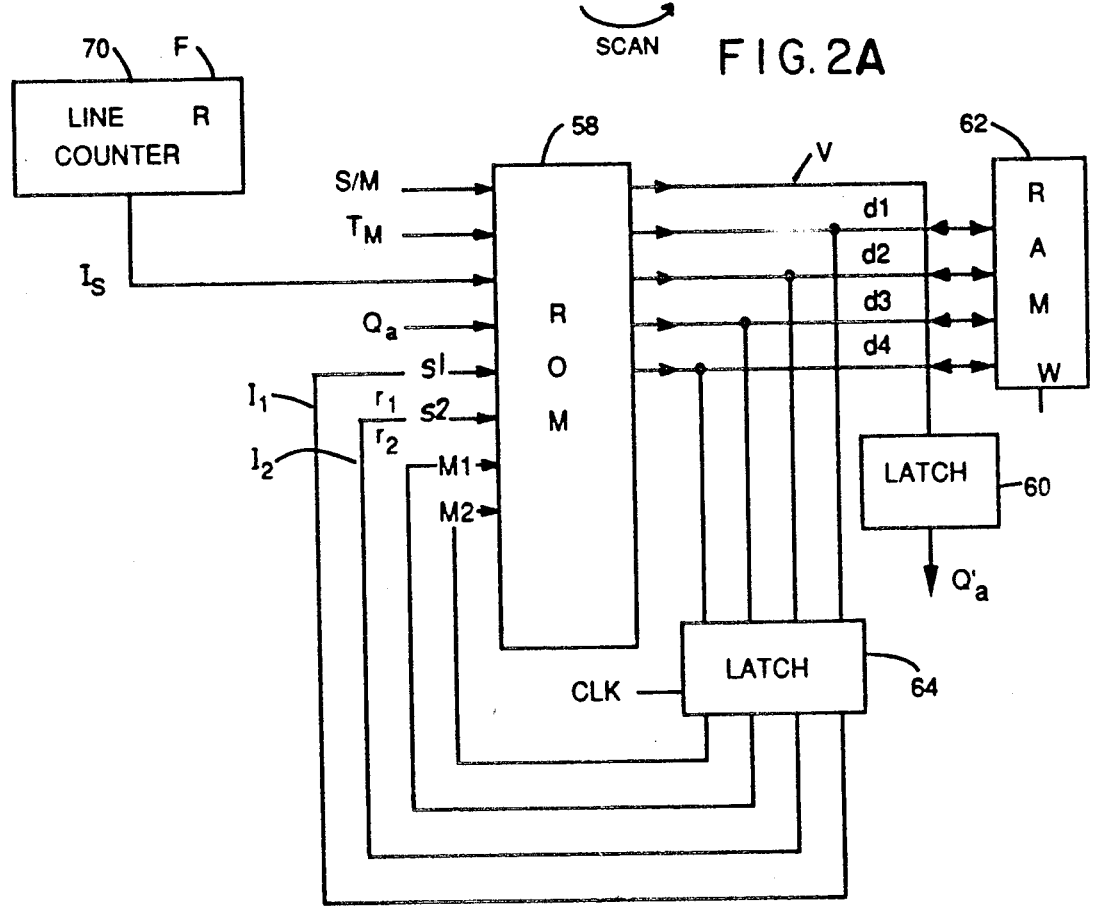
FIG. 2B is a schematic diagram of a majority vote circuit.
Figure 2C:
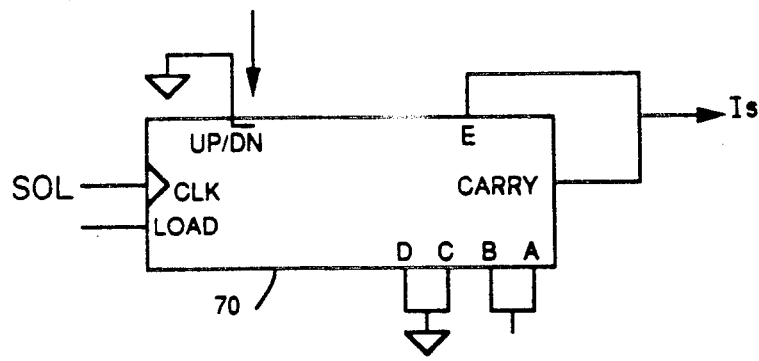
FIG. 2C is a schematic diagram of a circuit for generating the signal, Is, used in FIG. 2B.

FIG. 2B also has signals Im, M1, M2 and data lines d3 and d4 that are used in the same manner as the signals Is, S1, S2 and data lines d1 and d2 to derive a majority vote for M mode operation.

OBTAINING THE CROSS SECTIONAL AREA

Figure 3:
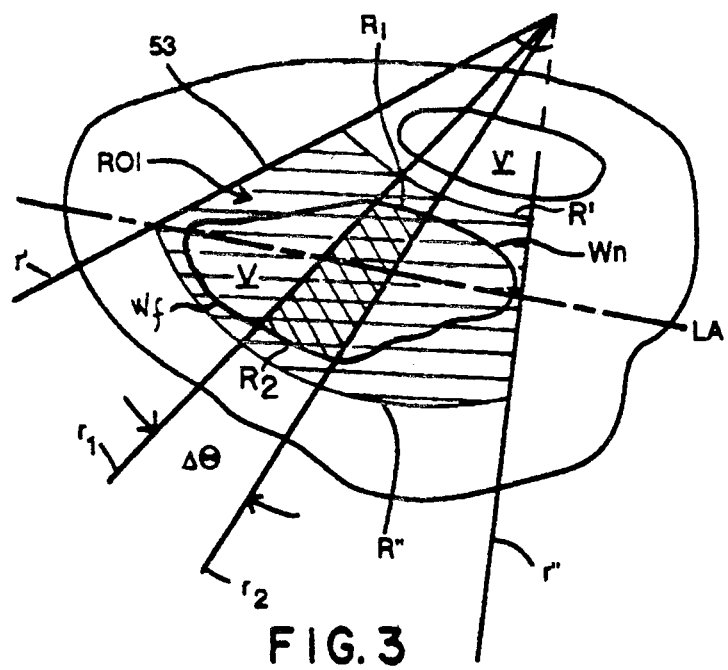
FIG. 3 is a cross section of a heart used in explaining how the cross sectional area and volume of a ventricle can be calculated in accordance with this invention when a sector scan is used.

Reference is now made to FIG. 3 for a general description of the method for obtaining a signal representing the cross sectional area of a ventricle in accordance with the invention. FIG. 3 shows the cross section of a heart per se as it would appear in the display 6 regardless of whether the scan lines for the scanner 2 are radial or parallel. It is assumed for the purpose of this discussion that the scan lines are radial, that they intersect the long axis LA of a ventricle V for which the cross sectional area is desired at nearly 90° and that at least some of them also pass through another ventricle V'. The ROI control 56 of FIG. 1 is adjusted in a manner to be explained so as to produce a signal O for producing a line in the image on the display 6 outlining the entire shaded region of interest, ROI, that includes the ventricle V but excludes the ventricle V'. The signals E from the ROI control 56 are used, as will be explained, to fully enable the circuits of the blocks 42, 52, and 54 of FIG. 1 only when signals are received corresponding to reflections from points within the region of interest, ROI, so that the areas and volumes derived relate only to the ventricle V.

Radial scan lines such as $r_1$ and $r_2$ are shown as passing through the near wall Wn of the ventricle V at a radius R1, then through the blood contained within the cavity of the ventricle and finally through the far wall Wf at a radius R2. The angle between the radial lines $r_1$ and $r_2$ is $\Delta\theta$. An incremental area bounded by $r_1$, $r_2$, Wn and Wf is indicated by the cross hatched shading. Its dimension along a radial line is $R_2-R_1$ and its average dimension along LA is $(R_2+R_1)/2$ so that its area is $$\frac{(R_2^2 - R_1^2)}{2} = \frac{\Delta\theta}{2} \int_{R_1}^{R_2} R dr$$

The total area of the cross section of the blood in the ventricle V is found by adding all the incremental areas.

Figure 3A:
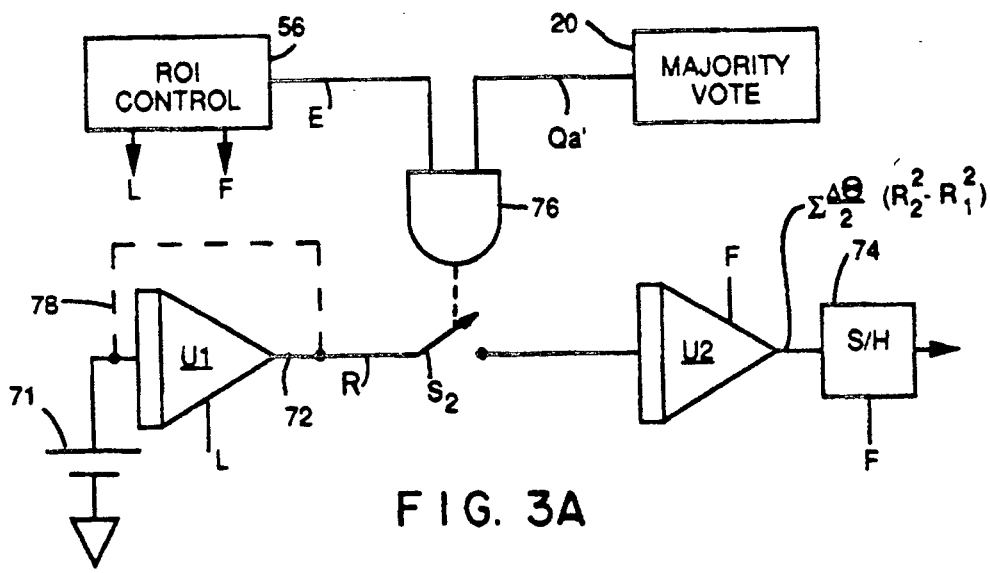
FIG. 3A is a schematic diagram of a circuit for determining the cross sectional area of a ventricle in accordance with this invention for both sector scan and parallel line scan.
Figure 3B:
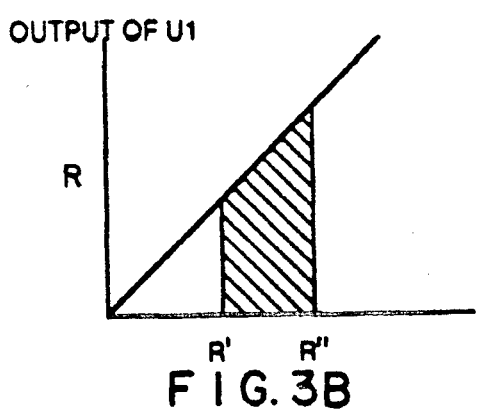
FIG. 3B illustrates the integration performed in the circuit of FIG. 3A.

FIG. 3A illustrates a circuit that can be used in the block 42 of FIG. 1 for calculating cross sectional area as just described. A D.C. voltage from a source 71 is applied to an integrator $U_1$ that is reset at the end of each scan line so as to produce a ramp voltage at its output terminal 72 as illustrated in FIG. 3B that is equal to the range R from which reflections are being received. The output of $U_1$ is coupled via a switch $S_2$ to the input of an integrator $U_2$ that is reset at the end of each frame, and a sample and hold device 74 that is reset at the end of each frame is coupled to the output of $U_2$. A signal E that is high only while signals are being received from reflectors within the region of interest, ROI, is produced by the ROI control 56 in a manner to be described and applied to one input of an AND gate 76, and a signal Q'a provided at the output of the majority vote circuit of FIG. 2B that is high only when reflections are from blood is applied to the other input. The output of the AND gate 76 will therefore only be high and close $S_2$ when reflections are received by the scanner 2 from blood within a selected region of interest ROI.

$U_1$ produces a ramp voltage such as shown in FIG. 3B having a value proportional to the radius R from which reflections are being received. If the integrator $U_2$ were reset at the end of each scan line and its gain properly adjusted, its output would be proportional to $$\Delta\theta \int_{R_1}^{R_2} RdR,$$

which is the incremental cross hatched area shown in FIG. 3. By further integrating this output signal over the period of a frame, a signal representing the cross sectional area of a ventricle such as V can be obtained. Both integrations are performed by $U_2$.

Figure 3C:
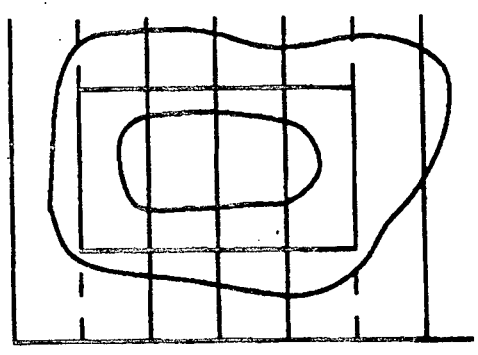
FIG. 3C is used in explaining the operation of the invention when parallel scan lines are used.

If the scan lines used by the scanner 2 are parallel as shown in FIG. 3C, the cross sectional area of a ventricle can be determined by omitting $U_1$ as indicated by a dashed line 78.

OBTAINING VOLUME BY ASSUMED SHAPES

In one embodiment of the invention, a signal corresponding to the real time variations in the volume of a ventricle is derived from the cross sectional area signal obtained as just described. The scanner 2 used to transmit and receive ultrasound is oriented with respect to the patient's body so that the area represented by the signal from the circuit 46 is either the long axis cross sectional area ALA or the short axis cross sectional area ASA as illustrated in FIG. 4A. The signal is then raised to the three halves power by the log and antilog circuits 44 and 46 of FIG. 1 or by the real time analog computational unit, ACU 48, and applied to the switching means contained within the dashed rectangle 50 that provides gains selected in accordance with the invention that are required to produce a signal that is representative of the volume of the ventricle.

Cardiologists have computed the volume of a ventricle by assuming that the shape of its blood containing cavity is an ellipsoid, a cylinder, a bullet or a half ellipsoid as respectively illustrated in FIGS. 4A-4D. Volume can be calculated for any of these assumed shapes on a real time basis by raising the signal for the cross sectional area, whether it be for ALA or ASA, to the 3/2 power and multiplying the value thus obtained by an appropriate coefficient including a function of the ratio a=ALA/ASA. ALA and ASA are only shown in FIG. 4A. In the expressions for the volume as set forth below, the letters indicate the shape and cross sectional area used e.g., VESA stands for the volume when the assumed shape is an ellipsoid and the short axis cross sectional area ASA is used, and VBLA stands for the volume when the assumed shape is a bullet and the long axis cross sectional area is used. In the following expressions "a"=ALA/ASA.

ellipsoid; FIG. 4A;

$$VESA = (2/3)(ASA\sqrt{4/\pi}) \cdot a \cdot (ASA)^{1/2} \qquad (1)$$
$$= (2/3) \cdot \sqrt{4/\pi} \cdot a \cdot (ASA)^{3/2}$$

ellipsoid; FIG. 4A;

$$VELA = 2/3 \cdot ALA/a \cdot \sqrt{4/\pi} \cdot \sqrt{a} \cdot ALA^{1/2} \qquad (2)$$
$$= 2/3 \sqrt{4/\pi} \cdot 1/\sqrt{a} \cdot (ALA)^{3/2}$$

Similarly:

cylinder; FIG. 4B;

$$VCSA = \sqrt{\pi/4} \cdot a \cdot (ASA)^{3/2} \qquad (3)$$

cylinder; FIG. 4B;

$$VCLA = \sqrt{\pi/4} \cdot 1/\sqrt{a} \cdot (ALA)^{3/2} \qquad (4)$$

bullet; FIG. 4C;

$$VBSA = 5/6 \cdot 8/(4+\pi) \cdot \sqrt{\pi/4} \cdot a \cdot (ASA)^{3/2} \qquad (5)$$

bullet; FIG. 4C;

$$VBLA = 5/6 \cdot 8/(4+\pi) \cdot \sqrt{\pi/4} \cdot 1/\sqrt{a} \cdot (ALA)^{3/2} \qquad (6)$$

half ellipsoid; FIG. 4D;

$$\frac{VESA}{2} = 4/3 \cdot \sqrt{4/\pi} \cdot a \cdot (ASA)^{3/2} \qquad (7)$$

half ellipsoid; FIG. 4D $$\frac{VELA}{2} = 4/3 \cdot \sqrt{4/\pi} \cdot 1/\sqrt{a} \cdot (ALA)^{3/2} \qquad (8)$$

From an examination of these expressions for volume it can be seen that there is a different coefficient for each assumed shape, i.e., whether it is an ellipsoid, cylinder, bullet or half ellipsoid, and for each cross sectional area, i.e., whether the cross sectional area measured by the circuit 42 is the short axis area, ASA, or the long axis area, ALA. The area ratio, a=(ALA/ASA), can be set as a constant from experience or may be determined from measurements. The time dependence of "a" can be programmed into the gain described below when the time relation is known.

If the scanner 2 of FIG. transmits and receives ultrasound oriented so that the circuit 42 measures the short axis cross sectional area, ASA, ganged switches S3 and S4 of the means 50 are placed in the positions shown, and a switch S5 is positioned so as to place one of gain control means G1 through G4 in the circuit depending on the shape a cardiologist wishes to assume for the blood containing cavity of the ventricle being examined. If, for example, it is assumed to be an ellipsoid, S5 is connected to G1 that provides a gain proportional to the coefficient of $(ASA)^{3/2}$ of the expression (1) i.e., $\frac{2}{3} \cdot \sqrt{4/\pi} \cdot a$. If a cylindrical shape is assumed, S5 will be connected to G2 that provides a gain proportional to the coefficient in the expression (3) i.e., $\frac{2}{3} \cdot \sqrt{\pi/4} \cdot a$.

On the other hand, if the scanner 2 is oriented so that the circuit 42 of FIG. 1 provides the cross sectional area ALA, the switches S3 and S4 are placed in the positions opposite to those shown and a switch S6 is connected to one of the gain control means G5 through G8 depending on the shape to be assumed for the blood containing cavity of the ventricle. For example, if an ellipsoid is assumed for the shape, S6 will place G5 in the circuit so as to provide a gain corresponding to the coefficient of $(ALA)^{3/2}$ in the expression (2) i.e., $\frac{2}{3} \cdot \sqrt{4/\pi} \cdot 1/\sqrt{a}$.

VOLUME BY SIMPSON'S RULE

Reference is again made to FIG. 3 for an explanation of the method by which the volume of a fluid filled cavity such as a ventricle of the heart may be calculated in accordance with this invention by use of Simpson's rule. In general, each incremental area such as the one indicated by the cross hatched shading in FIG. 3 is mathematically revolved about the axis LA to produce an incremental volume of revolution, and the incremental volumes are summed to attain the volume of the cavity or ventricle. The dimension of the cross hatched incremental area of FIG. 3 in a direction perpendicular to LA about which the area is to be revolved, is a radius $=(R_2-R_1)/2$, and its average length along LA is $(R_2+R_1)/2$ so that its incremental volume $\Delta V$ is $$\Delta V = \pi \frac{(R_2 - R_1)^2}{4} \cdot \frac{(R_2 + R_1)}{2} \cdot \Delta\theta \qquad (9)$$

which is the product of the average length of the incremental area along LA and the area of a circle having a diameter equal to the distance between R1 and R2.

By rearranging equation (9) we obtain the expression $$\Delta V = \frac{\pi}{4} \cdot (R_2 - R_1)(R_2^2 - R_1^2) \frac{\Delta\theta}{2} \qquad (10)$$

FIG. 5 is a schematic diagram of a circuit for deriving a signal representing the volume of a ventricle in accordance with equation 10. Components having the same function as in FIGS. 1 and 3A are similarly designated and will not be described again.

The components added to FIG. 3A are as follows. A line reset integrator U3 having the proper gain is connected to the output side of the switch S2 so as to perform the following operation.

$$\frac{\Delta\theta}{2} \int_{R_1}^{R_2} R dR = \Delta\theta/2 \cdot (R_2^2 - R_1^2) \qquad (11)$$

and derive a signal representing the cross hatched incremental area of FIG. 3. Note that this is the same as the portion of equation (10) to the right of the first parentheses. The rest of equation (10) can be derived by connecting a switch S7 that is ganged with the switch S2 between a source 80 of D.C. voltage and the input of a line reset integrator U4 and using the proper gain for U4. It is then only necessary to multiply the outputs of U3 and U4 in a multiplier M to produce a signal representing the incremental volume of revolution produced by revolving the incremental cross hatched area of FIG. 3 about the axis LA. A line reset sample and hold device 82 retains this signal while the next line is being scanned and applies it to a frame reset integrator U5 which produces a signal representing the volume of the ventricle V. This signal is then applied to a frame reset sample and hold device 84.

If the scanner 2 scans along parallel lines, as indicated in FIG. 3C, the incremental volume can be measured by a circuit in which the output of U4 is connected to both inputs of the multiplier M, and U3 is disconnected. The gain of the circuit can be adjusted to provide for the line spacing x so as to provide a signal $$\frac{\pi}{4}(R_2 - R_1)^2 \cdot \Delta x \qquad (12)$$

representing incremental volume which can be integrated in U5 to produce a signal representing the volume of a ventricle in accordance with Simpson's Rule.

M-MODE OPERATION

Reference is now made to FIG. 6 for a circuit that provides signals to be displayed when the system is operating in the M mode during which pulses of pressure waves are repeatedly transmitted along the same selected line by the scanner 2 and the amplitude of the reflection from each pulse is shown alongside amplitude of the previous one. The blood/tissue signal from the majority vote circuit 20 is applied via an invertor 86 and through switch S8 to the input of an integrator U6. S8 is controlled by the signal E from ROI control 56 which only occurs when the scanner 2 is receiving signals from within ROI. During the scanning of each line, U6 integrates the inverted low level D.C. signal at the output of the majority vote circuit 20 that occurs during reflections from blood so as to produce a signal indicative of the length of the scanned line, within the ventricle. The output of U6 is applied to a line reset sample and hold circuit 88 so as to provide a signal representing the length of a first scanning of a line between edges of a ventricle while the length of the next scan of the same line is being measured. This causes the output of the sample and hold circuit 88 to be a real time measurement of the changes in the diameter of the ventricle. The signals Im, M1 and M2 of the majority vote circuit 20 are derived in the same manner as the signals Is, S1 and S2.

OUTLINING AN R.O.I.

In FIG. 3 a region of interest, R.O.I. is shown for a sector scan in which the inner or top border is a line at a radius R', the outer or bottom border is a line at a radius R", the border in the left is along a radial line r' and the border on the right is along a radial line r". The following description relates to means that can be included in the ROI control 56 for generating a signal O that will form a line corresponding to these borders in the display of means 6 of FIG. 1.

FIG. 7 is a circuit for indicating the points along each radial scan line at which R' and R" that form the inner and outer borders of ROI occur, and FIG. 8 is a circuit for indicating the radial lines r' and r" on which the left and right borders of ROI occur. From these indications other circuits will form the signal ,O, that can respectively be used to form the various borders in the display 6.

FIG. 7 is comprised of a counter 90 and a counter 92 that load the digital counts, A, B,C and D for the desired values of R' and R" respectively at the beginning of each radial line in response to start of line pulses SOL shown in FIG. 9A. The carry outputs of the counters 90 and 92 go to a logic high as respectively shown by the pulses 94 of FIG. 9B and the pulses 96 of FIG. 9C. Clock pulses shown in FIG. 9D which may occur a thousand times during the scanning of each line are applied to the clock inputs of the counters 90 and 92. When the numbers of clock pulses reach the counts respectively loaded into the counters 90 and 92, their R' and R" outputs go to a low logic value as indicated by the edges 98 and 100 of the pulses 94 and 96. This occurs on every radial line.

In a similar manner, the circuit of FIG. 8 provides indications as to the occurrence of the radial lines r' and r". At the start of each frame indicated in FIG. 10A, selected line numbers A,B,C and D are respectively loaded into counters 102 and 104 of FIG. 8 so as to cause them to output a logic high as indicated by pulses 106 and 108 of FIGS. 10B and 10C respectively. Start of line pulses, SOL, shown in FIG. 10D, are applied to the clock inputs of the counters 102 and 104. When the number of lines reaches the number of counts respectively loaded into the counters 102 and 104, the r' and r" outputs go to a logic low value as indicated at the edges 110 and 112 of the pulses 106 and 108 respectively. The low logic value is retained for all subsequent lines of the frame.

Reference is no made to the circuit of FIG. 11 and the timing diagrams of FIG. 12A through FIG. 12H for an explanation of how a video signal for the inner border of ROI at a radius R' is generated. In this example only lines 3 through 6 are in ROI so that r'=3 and r"=6. The start of frame signals, SOF, FIG. 12A, are applied to the preset inputs of a J/$\overline{\text{K}}$ device 114 and a J/$\overline{\text{K}}$ device 116; the start of line signals, SOL, FIG. 12B, wherein the line numbers are indicated, are applied to the clock inputs; the r' signal from FIG. 8, shown in FIG. 12C, is applied to the K input of the J/$\overline{\text{K}}$ device 114, and the r" signal from FIG. 8, shown in FIG. 12D, is applied to the K input of the J/$\overline{\text{K}}$ device 116. The Q output of the device 114, shown in FIG. 12E, which is high if the line number is $\geq$r' as illustrated in FIG. 12E, is applied to one input of an AND gate 118, and the Q output of the device 116, shown in FIG. 12F, which is high if the line number is $\leq$r" as illustrated in FIG. 12F is applied to another input of the AND gate 118.

The signal R' for the inner border that is provided along each line by the circuit of FIG. 7, which is illustrated by the solid lines in FIG. 12G, is applied to a falling edge triggered monostable multivibrator 120, and its output is applied to another input of the AND gate 118. Therefore, if the line number is $\geq$r' and $\leq$r", a narrow pulse supplied by the multivibrator 120 causes the output of the AND gate 118 to become high, as shown in FIG. 12H. This occurs only on the consecutive lines three through six of FIG. 12B that are in ROI. The output of the AND gate 118 is for the inner border of ROI and is supplied to the O output of the ROI control 56 in a manner to be described.

Reference is made to the circuit of FIG. 13 and the timing diagrams of FIG. 12A through 12 G and I for an explanation of how a signal for the outer border of ROI at a radius R" is generated. The output Q from the J/$\overline{\text{K}}$ device 114 of FIG. 11 and the output Q of the J/$\overline{\text{K}}$ device 116 of FIG. 11 are connected to inputs of an AND gate 122, the signal R" from FIG. 7 is coupled to a falling edge triggered monostable multivibrator 124, and the output of the multivibrator 124 is connected to a third input of the AND gate 122 so as to produce narrow pulses at a radius R" indicated by dashed lines shown in FIG. 12G. Therefore, only those scan lines having a number $\geq$r' and $\leq$r" produce a narrow pulse at the output of AND gate 122. This occurs on consecutive lines three through six of FIG. 12B. The output of the AND gate 122 is for the outer border of ROI and is coupled to the output O of the ROI control 56.

FIG. 14 illustrates a circuit for generating a signal for forming the left border of ROI along the radial line r', which in this example is the third scan line of a frame. SOF signals are applied to the preset input of a J/$\overline{\text{K}}$ device 126, SOL signals are applied to its J input, and the output of a NAND gate 128 is applied to its K input. As shown in timing diagram 15G, the input to the K terminal is a negative pulse that occurs when r' of FIG. 8 is asserted. This pulse is derived by applying r' of FIG. 8 to the D input of a D-type flip flop 130, which is clocked by the point counter, and to an invertor 132. The output of the invertor 132 is the negative of r' and is applied to one input of the NAND gate 128, and the Q output of the D-type flip flop 130 is applied to the other input of the NAND gate 128. The point counter signals that occur along each scan line are applied to the clock input of J/$\overline{\text{K}}$ device 126 and its Q output is connected to one input of an AND gate 134. The signal R' of FIG. 7 is applied via an invertor 136 to another input of the AND gate 134, and the signal R" from FIG. 7 is applied to a third input of the AND gate.

In operation, the Q signal of FIG. 15H is high only during an entire line having a number equal to r', which starts at the trailing edge 138 of FIG. 15D, and, as can be seen from FIGS. 15J and 15K, R' and R" are both high only between the range of R' and R" within a scan line so that the output of the AND gate 134 is high only between the ranges of R' and R" on line r'.

Except for the substitution of r" for r' the circuit of FIG. 16 is the same as the circuit of FIG. 14. In this example r" is scan line 5. The corresponding components are designated with the same numerals primed. The circuit of FIG. 16 operates as illustrated in FIGS. 15A-C, I, J, K, M, N, and O. to produce a signal for the right border of ROI along the radial line r". The derivation of Q for FIG. 15N is not illustrated by waveforms but is similar to the derivation for Q in FIG. 15H. Note, however, that Q goes high at the fifth radial scan line r" rather than at the third radial line r' as in FIG. 14.

Figure 17:
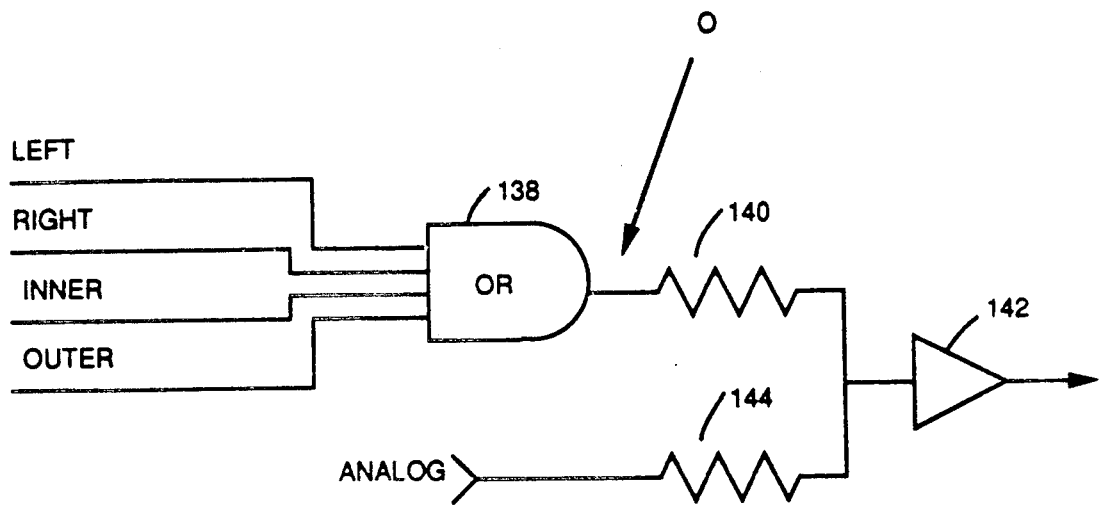
FIG. 17 is a schematic diagram of a circuit for combining the signals for the various borders of ROI with the video signals representing a cross sectional image.

FIG. 17 shows how the signals for the inner, outer, left, and right border lines respectively appearing at the outputs of the AND gates 118 of FIG. 11, 122 of FIG. 13, 134 of FIG. 14 and 134 of FIG. 16, are combined to produce an analog signal O at an output of the ROI controller 56 that can be applied to the display means 6 to outline the ROI. The outputs of these AND gates are applied to respective inputs of an OR gate 138 that is coupled to the display means 6 via a resistor 140 and a summing amplifier 142. The analog signals derived by the scanner 2 for the cross sectional image are coupled to the summing amplifier 144 via a resistor 146, and the values of these resistors are chosen such that the signal O from the ROI control 56 of FIG. 1 produces a maximum white when the output of the OR gate 138 is high and corresponds to the analog video when the output of OR gate 138 is low.

GENERATION OF ENABLING SIGNAL E

Figure 18:
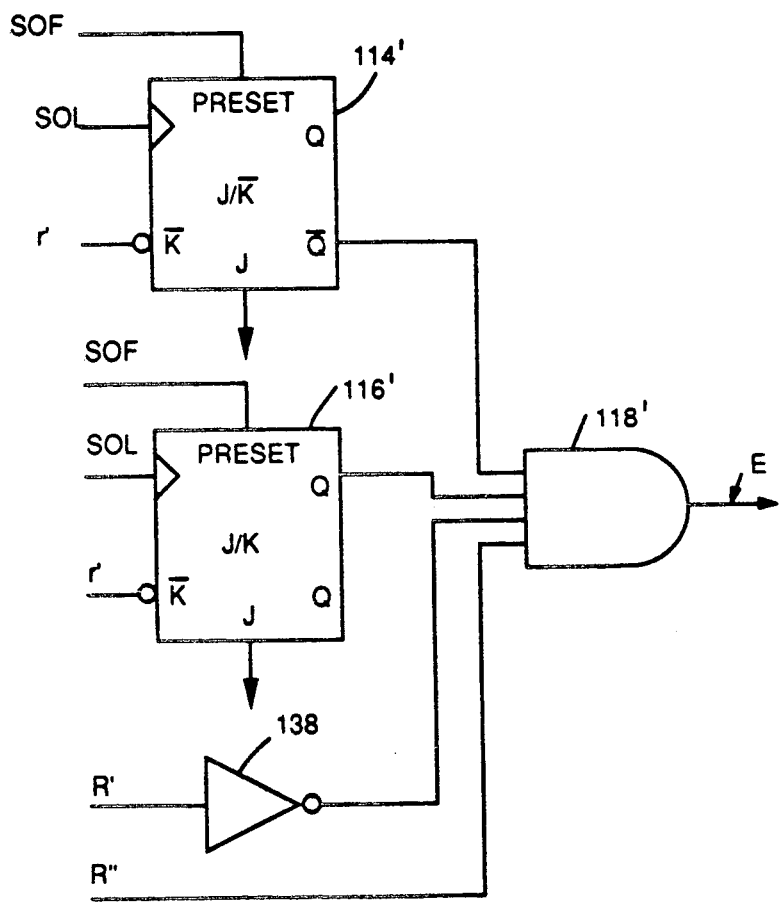
FIG. 18 is a schematic diagram of a circuit for providing an enabling signal, E, when reflections of the transmitted pulses of ultrasonic pressure waves are being received from points within ROI.

FIG. 18 schematically represents a circuit for generating the signal E provided by the ROI control 56 of FIG. 1 that is used to enable the circuits 42, 52 and 54 only when the electrical signals provided by the scanner 2 are in response to reflections from points within the region of interest, ROI. Components corresponding to those of FIG. 11 ar designated with numerals primed and operate in the same way. The J/K device 114' outputs a logic high at Q when the line number in a frame is $\geq$r' as shown by FIG. 12E, and the J/$\overline{\text{K}}$ device 116' outputs a logic high when the line number in a frame is $\leq$r" as shown in FIG. 12F. These outputs are applied to the AND gate 118'. The signal R' from the circuit of FIG. 7 is applied to an invertor 148 to produce R' as shown in FIG. 15J. The signals R' and R" are applied to the AND gate 118. Thus the AND gate 118' outputs a signal E that is a logic high when echoes are arriving at the scanner 2 from within ROI. Application of the signal E to the circuits 42, 52 and 54 enables them only when such reflections are being received.

GENERAL COMMENT

Although the preferred embodiment described has been directed to determining the edge between tissue and blood in a ventricle, it could also be applied to determining the edge or border of other fluid-filled cavities, or between two tissues such as healthy tissue and tissue in a tumor. Furthermore, by using two comparators having different reference values applied to them, the edges between three tissues can be identified. While this embodiment was realized with hardware elements, one of ordinary skill could also implement the teachings of this invention in software or firmware form through the use of such logic elements as general or special purpose computers, programmable logic arrays, RAMs, or ROMs.

Whereas integrated backscatter is usually derived from r.f. signals, a signal proportioned to integrated backscatter could be derived from a full scale non-compressed video signal.

The preferred embodiment has included a scanner as the source of signals, but other sources could be used such as a recording on a disc or tape, but the procedure prior to the tissue indicator (comparator) would depend on whether the recording is r.f., compressed video or full scale video. In any case, better results are obtained by using the majority vote circuit. Preferably, the signal processing should be the derivation of the amplitude of the integrated backscatter from the r.f.

The invention has been described in a system using a scanner, but the signals used might be numbers at the respective pixels indicating the value of a given characteristic, and an edge or border could be detected in the same way.

We claim:

1. Apparatus for deriving a signal corresponding to the incremental area that lies between the edges of a fluid filled cavity and between successive scan lines comprising:
    means for transmitting pulses of ultrasonic pressure waves along scan lines of a frame in sequence,
    means for deriving electrical signals from the reflections of said pulses of pressure waves from reflectors in each scan line,
    a tissue/fluid indicator circuit responsive to said electrical signals for producing at each of a plurality of ranges a first output value when the reflections are from tissue and a second output value when the reflections are from fluid,
    means synchronized with said means for transmitting pulses for producing a voltage during a scan line such that integration thereof provides a signal corresponding to one of the area between successive radial scan lines and the area between successive parallel scan lines, and
    means for integrating said voltage only when said tissue/fluid indicator circuit produces said second output value so as to produce a first output signal representing said incremental area.

2. Apparatus as set forth in claim 1 further comprising: a majority vote circuit coupled between said tissue/fluid indicator circuit and said means for integrating so as to provide to said means for integrating the output value of said tissue/fluid circuit that occurred in a majority of a given number of previous scan lines at each of said ranges.

3. Apparatus as set forth in claim 1 wherein said means for producing said voltage is comprised of an integrator having a D.C. voltage applied to its input.

4. Apparatus as set forth in claim 3 further comprising means for integrating successive first output signals so as to derive a second output signal representing a cross sectional area of said cavity.

5. Apparatus as set forth in claim 1 wherein said means for producing said voltage is a source of D.C. voltage.

6. Apparatus as set forth in claim 5 further comprising means for integrating successive first output signals so as to derive a second output signal representing a cross sectional area of said cavity.

7. Apparatus as set forth in claim 1 wherein said means for transmitting pulses of ultrasonic pressure waves produces pulses at the start of each line and pulses at the start of each frame further comprising:
    means responsive to said pulses at the start of each frame and the pulses at the start of each line for deriving a signal defining the borders of a region of interest in each frame.

8. Apparatus as set forth in claim 7 further comprising: means responsive to said pulses at the start of each frame and the pulses at the start of each line for producing an enabling signal only when the electrical signals are in response to reflections of the transmitted pulses of ultrasonic pressure waves from points within said region of interest.

9. Apparatus as set forth in claim 1 wherein said cavity is a ventricle and said means for transmitting pulses of ultrasonic pressure waves transmits the pulses in directions nearly perpendicular to the long axis of said ventricle, said apparatus further comprising:
    means for producing signals respectively representing incremental volumes that are the product of the area of a circle having a diameter equal to the range during which said first output values occur and the average dimension of the corresponding incremental area along the long axis of said cavity.

10. Apparatus as set forth in claim 9 further comprising:
    means for summing said signals representing incremental volumes.

11. Apparatus as set forth in claim 1 further comprising
    means for integrating successive first output signals so as to derive a second output signal representing a cross sectional area of said cavity.

12. Apparatus as set forth in claim 11 wherein:
    said cavity is a ventricle of the heart of a subject and said means for transmitting pulses of ultrasonic pressure waves transmits them along scan lines that are nearly perpendicular to one of the long axis and short axis of said ventricle so that said cross sectional area signal represents one of the long axis cross sectional area (ALS) and the short axis cross sectional area (ASA) of said ventricle, said apparatus further comprising:
    means for raising said second output signal to 3/2 power, and
    means for multiplying the result thus obtained by a function of a ratio "a" of the long axis and short axis cross sectional areas, ALA and ASA respectively, and a coefficient depending on an assumed shape of said cavity so as to produce a third output signal corresponding to the volume of said cavity.

13. Apparatus as set forth in claim 12 wherein: said coefficient is $$(2/3) \cdot \sqrt{4/\pi} \cdot a$$

14. Apparatus as set forth in claim 12 wherein: said coefficient is $$(2/3) \cdot \sqrt{4/\pi} \cdot 1/\sqrt{a}$$

15. Apparatus as set forth in claim 12 wherein: said coefficient is $$\sqrt{\pi/4} \cdot a$$

16. Apparatus as set forth in claim 12 wherein: said coefficient is $$\sqrt{\pi/4} \cdot 1/\sqrt{a}$$

17. Apparatus as set forth in claim 12 wherein: said coefficient is $$5/6 \cdot 8/(4 + \pi) \cdot \sqrt{\pi/4} \cdot a$$

18. Apparatus as set forth in claim 12 wherein: said coefficient is $$5/6 \cdot 8/(4 + \pi) \cdot \sqrt{\pi/4} \cdot 1/\sqrt{a}$$

19. Apparatus as set forth in claim 12 wherein: said coefficient is $$4/3 \cdot \sqrt{4/\pi} \cdot a$$

20. Apparatus as set forth in claim 12 wherein: said coefficient is $$4/3 \cdot \sqrt{4/\pi} \cdot 1/\sqrt{a}$$

21. Apparatus for deriving a signal corresponding to the volume of a fluid filled cavity formed within tissue comprising:

transducer means for successively transmitting pulses of ultrasonic pressure waves along successive radial scan lines and for producing electrical waves corresponding to reflections of said pulses from reflectors along said scan lines, means responsive to said electrical waves for producing indications as to when pulses causing them are reflected from fluid, a first integrator having an input and an output, means for applying a D.C. voltage to said input, a second integrator having an input and an output, switching means for coupling the output of said first integrator to the input of said second integrator in response to said indication, a third integrator having an input and an output, means for applying a D.C. voltage to the input of said third integrator in response to said indication, a multiplier having two inputs and an output, said latter inputs being respectively coupled to the outputs of said second and third integrators, means for resetting said first, second and third integrators after reflections of each pulse have been received from maximum range, and means coupled to the output of said multiplier for summing the signals appearing therein in response to a given number of pulses.

22. Apparatus for deriving a signal corresponding to the volume of a fluid filled cavity formed within tissue comprising:

transducer means for transmitting pulses of ultrasonic pressure waves along successive parallel scan lines and for producing electrical waves corresponding to reflections of said pulses from reflectors along said scan lines, means responsive to said electrical waves for producing indications as to when pulses causing them are reflected from fluid, a first integrator having an input and an output, means for resetting said first integrator after the reflections of each pulse from a maximum range have reached said transducer means, means for coupling a D.C. voltage to said input in response to said indications, a multiplier having two inputs, means for coupling the output of said first integrator to each of said inputs of said multiplier, a second integrator having an input and an output, means for resetting said second integrator after a given number of pulses have been transmitted, and means for coupling the input of said second integrator to the output of said multiplier whereby a signal is produced at the output of said second integrator representing the volume of said cavity.

23. In a system having a scanner for transmitting pulses of ultrasound into a body along successive scan lines and for producing at an output thereof first signals from reflections of the pulses from reflectors along the scan lines, apparatus for deriving second signals indicating the locations along the lines of the edges of a cavity within the body comprising:

indicator means for producing a third signal when a signal applied to it exceeds a given reference value and a fourth signal when a signal applied to it is less than the given reference value, means for coupling said indicator means to said output, and majority vote means for producing a fourth signal when said second signal occurs at the same range in a majority of a current line and a given number of previous lines and a fifth signal when said third signal occurs on the same range of a majority of the current line and the said given number of previous lines, and edge indicating means for producing a fifth signal when said third and fourth signals occur in succession along a current line.

24. In a system as set forth in claim 23, means for deriving a signal representing integrated backscatter from said first signals included in said means for coupling so as to apply the signal representing integrated backscatter to said majority vote means.

25. In a system as set forth in claim 23, means for coupling said first signals appearing at said output to said indicator means.

26. Apparatus for identifying the border between adjacent matter in an image of a cross section of a living body comprising:
- a source of signals representing a characteristic of matter at points in said image;
- signal processing means coupled to said source for producing processed signals;
- a threshold detector having first and second inputs and an output;
- means for coupling said processed signals to said first input of said threshold detector;
- means for applying a reference value to said second input of said threshold detector, said threshold detector producing a first level at its output when the processed signal exceeds the reference value and a second level at its output when a processed signal is less than the reference value;
- means responsive to said levels for a plurality of contiguous points in the image for producing a level corresponding to the majority of said first and second levels; and
- means for producing a signal representing an edge at each point where said majority shifts from one of said first and second levels to the other.

27. Apparatus as set forth in claim 26 wherein:
- said signals represent the amplitude of reflection of a pulse of acoustic pressure waves from points along a scan line; and
- said signal processing means produces processed signals that represent the amplitude of the integrated backscatter of said signals.

28. Apparatus as set forth in claim 27 wherein means are provided for reproducing the signal representing an edge in said image.

* * * * *